United States Patent [19]

Lam et al.

[11] Patent Number: 5,616,122
[45] Date of Patent: *Apr. 1, 1997

[54] METHODS AND COMPOSITIONS FOR PREVENTING SECONDARY CATARACTS

[75] Inventors: Dominic M. Lam; Peter J. Kelleher, both of The Woodlands, Tex.

[73] Assignee: Baylor College of Medicine, Houston, Tex.

[*] Notice: The term of this patent shall not extend beyond the expiration date of Pat. No. 4,871,350.

[21] Appl. No.: 517,364

[22] Filed: May 1, 1990

Related U.S. Application Data

[63] Continuation-in-part of Ser. No. 204,168, Jun. 8, 1988, Pat. No. 4,871,350, which is a continuation-in-part of Ser. No. 927,318, Nov. 4, 1986, abandoned.

[51] Int. Cl.$^6$ ................................................. A61M 31/00
[52] U.S. Cl. ........................................ 604/49; 514/912
[58] Field of Search ............... 604/20, 49; 530/387–389, 530/849; 514/912–915; 424/85.91; 436/547–548

[56] References Cited

U.S. PATENT DOCUMENTS

| | | |
|---|---|---|
| 4,340,535 | 7/1982 | Voisin et al. . |
| 4,432,751 | 2/1984 | Emery et al. .............................. 604/49 |
| 4,590,071 | 5/1981 | Scannon et al. . |
| 4,698,420 | 2/1985 | Urnovitz . |
| 4,871,350 | 10/1989 | Lam et al. ................................. 604/49 |
| 4,909,784 | 3/1990 | Dubroff ..................................... 604/49 |

FOREIGN PATENT DOCUMENTS

| | | |
|---|---|---|
| 44167 | 1/1982 | European Pat. Off. . |
| 173648 | 5/1986 | European Pat. Off. . |
| 140109 | 8/1986 | European Pat. Off. . |
| 88/02594 | 4/1908 | WIPO . |
| 89/08474 | 9/1989 | WIPO . |

OTHER PUBLICATIONS

"Use of Immunotoxin to Inhibit Proliferating Human Corneal Endothelium" by Fulcher et al. *Investigative Ophthalmology & Visual Science* (1988).

"Methotrexate–Anticollagen Conjugate Inhibits In Vitro Lens Cell Outgrowth" by Hansen et al., *Investigative Ophthalmology & Visual Science* (1987) 28:1206–1209.

"Use of Immunotoxin to Inhibit Proliferating Human Corneal Endothelium" by Fulcher et al. *Investigative Ophthalmology & Visual Science* (1988) 29:755–759.

*Primary Examiner*—Randall L. Green
*Assistant Examiner*—Ronald K. Stright, Jr.
*Attorney, Agent, or Firm*—Rae-Venter Law Group a professional law corporation

[57] ABSTRACT

Novel methods and compositions are provided for preventing secondary cataracts. A cytotoxic agent is employed which is introduced into the anterior chamber of the eye to inhibit proliferation of remnant tens epithelial cells after extracapsular cataract extraction. Desirably a non-cytotoxic agent crossreactive with the cytotoxic agent is introduced prior to introduction of the cytotoxic agent. The agents can be provided as kits.

11 Claims, No Drawings

METHODS AND COMPOSITIONS FOR PREVENTING SECONDARY CATARACTS

This application is a continuation-in-part of U.S. Ser. No. 204,168, filed Jun. 8, 1988 now U.S. Pat. No. 4,871,350 issued Oct. 3, 1989 which is a continuation-in-part of U.S. Ser. No. 927,318, filed Nov. 4, 1986, now abandoned which disclosures are incorporated herein by reference.

INTRODUCTION

1. Technical Field

The field concerns methods and compositions for inhibiting secondary cataracts using cytotoxic compositions which react specifically with lens epithelial cells.

2. Background

An intact posterior lens capsule is required for implantation of a wide variety of intraocular lenses. The surgical technique that preserves the posterior lens capsule, and which is found used in the treatment of cataracts, is generically termed extracapsular cataract extraction. The technique includes extracapsular cataract extraction, phacoemulsification, endocapsular extraction, intercapsular extraction and Dodick laser phacolysis. Newer methods of extracapsular cataract extraction under development, such as the Kelman phaco fly, would remove a cataract through a puncture of the lens capsule and refill the lens capsule bag with a flexible substance or an inflatable lens to restore vision and to preserve or restore natural accommodation.

Extracapsular cataract extraction is a desirable method for removing cataracts due to a lower incidence of post-operative complications such as cystoid macular edema and retinal detachment. However, the surgical method is accompanied by a significant incidence of posterior lens capsule opacification, which may require additional surgical procedures such as posterior capsulotomy or polishing of the posterior lens capsule to provide good vision.

The pathogenesis of posterior lens capsule opacification after extracapsular cataract extraction is reported to be due to proliferation of remnant lens epithelial cells on the posterior lens capsule to form abortive lens "fibers" and "bladder" cells (i.e., Elschnig's pearls). Various cytotoxic agents, including vincristine and vinblastine are reported to inhibit the secondary cataract formation or posterior lens capsule opacification. Radiation has also been tried and was reported to be promising. Methotrexate and retinoic acid have been reported for instillation in the anterior chamber of the eye to kill residual lens epithelial cells and thus prevent posterior lens capsule opacification. These methods are relatively non-specific and can damage and/or kill other cells in addition to the lens epithelial cells.

It would be of interest to develop substantially specific methods for preventing secondary cataract formation or posterior lens capsule opacification thereby avoiding potential side effects due to the use of cytotoxic agents. The unique anatomical location of the various cell types during cataract surgery makes possible the use of cytotoxic agents which are substantially specific for epithelial cells present in the posterior chamber of the eye. The method may be used in combination with pretreatment with a non-cytotoxic agent having the same specificity for lens epithelial cells as the cytotoxic agent.

Relevant Literature

Production of monoclonal antibodies has been described. See, for example, *Monoclonal Antibodies*, eds. Roger H. Kennett, Thomas J. McKearn, Kathleen B. Bechtol, Plenum Press, New York, 1980; *Nature* (1975) 256:495–497; U.S. Pat. Nos. 4,271,145; 4,196,265; 4,172,124; 4,195,125; 4,262,090; and 4,294,927. See also, U.S. Pat. No. 4,432,751, which discloses the combination of monoclonal antibodies and complement for preventing secondary cataracts.

SUMMARY OF THE INVENTION

Methods and compositions are provided for inhibiting posterior lens capsule opacification after extracapsular cataract extraction. The methods involve using cytotoxic agents specific for epithelial cells and introducing them into the anterior chamber of the eye, the posterior chamber of the eye and/or the residual lens capsule concurrently with or subsequent to the extracapsular cataract extraction. Of particular interest is introducing non-cytotoxic agents into the anterior and/or posterior chamber(s) prior to the introduction of the cytotoxic agents, where the non-cytotoxic and cytotoxic agents have substantially the same binding affinity for epithelial cells. The method can be used for preventing opacification of the posterior lens capsule. Also provided are compositions and methods for testing the cytotoxic agents.

DESCRIPTION OF THE SPECIFIC EMBODIMENTS

Methods and compositions are provided for inhibiting proliferation of remnant lens epithelial cells after extracapsular extraction. The method comprises introducing into the anterior chamber of the eye, the posterior chamber of the eye and/or the residual lens capsule, cytotoxic agents at least substantially specific for epithelial cells, so as to at least substantially inhibit the proliferation of the lens epithelial cells. The cytotoxic agents are at least substantially specific for the lens epithelial cells in that they bind to a cell surface moiety on the lens epithelial cell with high affinity and have low or no cross-reactivity with other cells found in the anterior chamber, such as fibroblasts, melanocytes, corneal endothelial cells, etc., desirably also other epithelial cells, e.g., ciliary epithelial cells, and corneal epithelial cells. Preferably, prior to introduction of the cytotoxic agent and prior to the extracapsular cataract extraction, a non-cytotoxic agent is introduced into the anterior chamber, where the non-cytotoxic agent is cross-reactive with or has substantially the same binding specificity as the cytotoxic agent, so as to bind to any cells in the anterior chamber which are in contact with the anterior chamber having homologous determinant or antigenic sites. By "high affinity" is intended a $K_d$ (dissociation constant) of at least $10^{-7}$M, preferably at least $10^{-9}$M, most preferably at least $10^{-10}$M.

The cytotoxic agent is a conjugate of a protein macromolecule capable of binding at least substantially specifically to epithelial cells, particularly lens epithelial cells, as compared to other cells which may be present in or in contact with the anterior or posterior chamber of the eye. For the most part, cytotoxic compositions will be conjugates of a monoclonal antibody or its equivalent with a cytotoxic agent. The monoclonal antibody may be produced as a result of hybridoma formation and expression by the hybridoma, whether in culture or present as ascites, a monoclonal antibody fragment, such as Fab, F(ab')$_2$, Fv, a recombinant variable region, a T-cell receptor, or the like. The monoclonal antibodies and receptors may be any mammalian species, including murine, rabbit, human or the like, or combinations thereof, such as chimeric antibodies, having a human constant region and a mouse or other mammalian source variable region. The antibodies may be any class or subclass, such as IgA, IgD, IgG, IgM, and may include IgG1, 2a, 2b, or 3 or the human equivalents thereof. The monoclonal antibodies may be derived either from a simple hybridoma cell line or may be a mixture or "cocktail" of two or more monoclonal antibodies derived from different hybridoma cell lines, where the antibodies would bind to the same or different antigenic moieties on the epithelial cells.

The methods for preparing the monoclonal antibodies are well established as evidenced by the numerous references described above (see "Relevant Literature"). An animal is hyperimmunized with a suitable immunogen, with or without addition of adjuvant. Various epithelial cells may be used as the immunogen, particularly human epithelial cells, including lens epithelial cells and tumor cells originating from epithelial cells, for example HeLa cells, although other species may find use, e.g., primates as well as interspecies recombinant cells. Whole cells are preferred, however homogenates, membrane fragments or the like, can be used. The source of the cells includes cells in tissue culture, surgical specimens such as tissues removed during cataract surgery, biopsy specimens, and the like.

In accordance with the subject invention, a mammal, which can be a mouse or other mammal, is hyperimmunized with the immunogen. Methods of immunization are well known and are amply described in the literature. The immunogenic material, generally about $10^5$ to about $10^6$ cells or cell equivalents, is injected with or without adjuvant into the mammal, or by repeated injections over relatively short periods of time. To ensure the hyperimmunization of the animal, 2–6 subsequent booster injections are administered. The animals are then killed, usually within 1–5 days after the last injection, when it has been determined that a suitable titer of antibody has been obtained. Antibody-producing cells such as spleen cells or lymphocytes from the immunized animal are removed and immortalized.

The method of cell-fusion is not a critical portion of this invention and various techniques may be employed. Generally a nonionic detergent, for example polyethyleneglycol (PEG), is used as the fusigen. The antibody-producing cells, for example spleen cells and myeloma cells are combined in the presence of a non-ionic detergent conveniently PEG1540 and other additives, for example, serum-free Dulbeccos modified Eagles medium (SF-DMEM) for approximately 5 minutes. The excess nonionic detergent is then removed by washing the cells. The cells are promptly dispensed into small culture wells at a relatively low density, ranging from about $1\times10^4$/well to about $5\times10^5$/well in appropriate medium, commonly a selective medium comprising hypoxanthine, and aminopterin and thvmidine (HAT) medium.

After a sufficient period, usually one to two weeks, colonies of hybrids are observed. The colonies are then screened for antibodies which bind at least substantially specifically to epithelial cells. To identify hybridomas of interest, antibodies secreted by the immortalized cells are screened to identify the clones that secrete antibodies of the desired specificity. Screening of the hybridoma clones may be by binding to epithelial cells, particularly lens epithelial cells, using an enzyme linked immunosorbent assay (ELISA) assay. Other screening methods include radioimmunoassay and immunohistochemical staining of frozen sections of ocular tissue.

To obtain hybridoma cell lines secreting monoclonal antibodies directed to a single antigenetic determinant associated with epithelial cells, the hybridoma cells may be cloned using, for example, limiting dilution. The stage at which the cells may be cloned is not critical to the invention, and may be before identification of colonies secreting antibodies of interest, or later. However, to avoid overgrowth of antibody producing cells with non-antibody producing cells, the colonies are preferably cloned as soon after fusion as practicable.

Once colonies producing the desired antibodies have been identified, the colonies may be perpetuated to provide for a continual source of the desired antibodies. For large-scale production of antibodies, the hybridomas may be introduced into the peritoneal cavity of a mouse or other mammal and grown as ascites tumors. Antibodies may then be isolated from the ascites fluid. Alternate methods for large-scale production of monoclonal antibodies include introducing subcutaneous tumors using the method described and collecting blood from the animal. The hybridoma cells can also be grown on a large-scale in cell culture. Where the cells secrete the antibodies into the growth medium, the conditioned growth medium containing the antibodies can be collected for antibody isolation. Where the hybridoma cells do not secrete the antibodies, the cells may be collected, lysed using conventional means, and antibody purified from the cell lysate. Methods of purifying monoclonal antibodies are well known to those skilled in the art.

The monoclonal antibodies obtained may be isolated and modified by truncating the constant region by various peptidase digestions. The monoclonal antibodies may be reduced to provide for Fab fragments with available mercaptan sites for conjugation to other compositions. T-cell receptors may be obtained as described in WO85/03947.

The binding compositions having specificity for epithelial cells, may be joined to a wide variety of toxic agents which may be derived from microorganism or plant sources. Of particular interest are the toxic subunits of naturally occurring toxins, such as ricin, abrin, diphtheria toxin, etc. See for example Oeltmann and Heath, *J. Biol. Chem.* (1979) 254:1022–1027; Yule and Neville Jr., *Proc. Natl. Acad. Sci. USA* (1980) 77:5483–5486; Gilliland et al., *Proc. Natl. Acad, Sci. USA* (1978) 75:5319–5323; U.S. Pat. No. 4,379, 145; GB2034324 and Masuho et al., *Biochem. Biophys. Res. Comun.* (1979) 90:320–326; and Blythman, *Nature* (1981) 290:145, the relevant disclosures of which are incorporated herein by reference.

Illustrative toxin A-chains or similarly effective moieties include diphtheria toxin A-chains, enzymatically active proteolytic fragments from *Pseudomonas aeruginosa* exotoxin-A, ricin A-chain, abrin A-chain, modeccin A-chain, and proteins found in various plants having similar activity, such as the plants *Gelonium multiflorum, Phytolacca americana, Croton tiglium, Jatrophaa curcas, Momordic charantia,* wheat germ, the toxin saporin from *Saponaria officinalis* (Thorpe et al., *J. Natl. Cancer Inst.* (1985) 75:151), and the Chinese cucumber toxin, trichosanthin (Yeung et. al., *Intl. J. of Peptide Protein Res.* (1985) 27:325–333). Of particular interest is the ricin A-chain. Also, mutant species of the toxins of the species may be used, such as CRM45 (Boquet et al., *Proc. Natl. Acad. Sci. USA* (1976) 73:4449–4453).

The toxic agents and moiety providing for binding to the epithelial cells may be linked, usually by a bond which is clearable cytoplasmically. Convenient linkages include disulfide, particularly where the toxic agent has an intrinsic sulfur, or other links, such as peptide links, urea links, thioethers, imines, amides, imides, amidines, etc. Functional groups which may find employment include carboxylic acid groups, amino groups, imines, aldehydes, isocyanates, mercaptans, olefins, or the like. In addition, more complex linking groups can be employed, where a group may be bound to one of the moieties in the conjugate to provide for convenient linkage to an intrinsic group of the other moiety. For example, the N-hydroxysuccinimide ester of m-maleimidoylbenzoic acid may be employed to prepare an amide of the toxin, which may then be linked through an available sulfur atom on the monoclonal antibody to provide a thioether.

Exemplary cytotoxic agents may have the following formula:

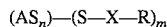

$$(AS_n)-(S-X-R)_m$$

wherein:

$AS_n$ indicates the toxic agent having one or more sulfur groups as part of the agent; n is 1 to the number of sulfur groups present in the toxic agent which are present as available mercaptide groups, generally being up to about 4; R is a monoclonal antibody or derivative thereof; and m is 1 up to n, usually being from 1 to 2; and X is a linking group and may be a bond or a group of from about 1 to 20, usually 1 to 12 atoms other than hydrogen, which include carbon, nitrogen, oxygen and sulfur. Sulfur will normally be bonded to carbon, particularly aliphatically saturated. X may be aliphatic, alicyclic, aromatic, heterocyclic or combinations thereof generally having from 0 to 6, more usually from about 0 to 4, preferably about 1 to 4 heteroatoms, wherein oxygen and sulfur are present as oxo or non-oxo-carbonyl or the thio analogs thereof, or ether (including thioether), and nitrogen is present as amino or amido. For the most part the heteroatoms will be bonded solely to carbon.

Illustrative groups linking the disulfide include aminoethylene 3-propanyl methylene carbonyl, α-succinimidyl, 3-propylenethiocarbonyl. The groups which may be used are for the most part conventional groups providing for a disulfide linkage. The disulfide compound is one which is capable of reacting with the cell-specific ligand, whereby a mercaptide group may be displaced from the disulfide, resulting in a new disulfide linkage between the toxic agent and the ligand. For the most part, the linkages will be aliphatic of from about 1 to 6 carbon atoms, providing for an amide bond to the receptor, although this is primarily a matter of convenience, not necessary to the operability of the subject compositions.

Other toxic agents may also be used, such as bismuth non-diffusively linked to the monoclonal antibodies or receptors as described by Waldman, *J. Amer. Med. Assoc.*

Alternatively, liposomes may be linked to the monoclonal antibodies or receptors, where the liposomes contain various cytotoxic agents, such as methotrexate, 5-fluorouracil, any of the above toxins, or the like. See, for example, Szoka and Papahadjopoulos, *Proc. Natl. Acad. Sci. USA* (1978) 75:4194–4198 and Szoka et al., *Biochem. et Biophys. Acta.* (1980) 601:559–571 for the preparation of liposomes, which disclosures are incorporated herein by reference. Linking of antibodies to the liposome has been amply described in the literature, see for example Heath et al., *Proc. Natl. Acad. Sci. USA* (1983) 80:1377–1381 and Leserman et al., *Nature* (1981) 293:226–228, which disclosures are incorporated herein by reference.

Other cytotoxic agents conjugated to the binding moiety may also be employed in conjunction with the process of this invention. The conjugate generally will be sufficient to provide the cytotoxic effect without the addition of ancillary agents, but could be used with other agents such as lysomotropic amines, carboxylic, ionophores and calmodulin inhibitors. Examples include ammonium chloride, methylamine, chloroquine, monensin and verapamil. For descriptions of these agents, see for example, Casellas, et. al., *Immunotoxin* (1988) Kluwer Academic Publishers; Myers, et. al., *Blood* (1984) 63:1178–1184; Casellas, *J. Biol. Chem.* (1984) 259:9359–9364; and Akiyama *J. Cell. Physiol.* (1984) 120:271–279.

The cytotoxicity of the conjugate may be determined by evaluating the effect of the conjugate comprising the toxic agent and the moiety providing for binding to epithelial cells by incubation with a culture comprising epithelial cells, particularly lens epithelial cells. It is preferable to test the cytotoxic agent using cells as similar as possible to the intended target cell type since the sensitivity of various cell types to cytotoxic agents may vary significantly. Tumor cells may be more sensitive to toxin than normal cells from the same species (Pappenheimer et al., *Journal of Experiamemtal Medicine* (1968) 127:1073–1086). Likewise, primary cells may have a different sensitivity to a given cytotoxic agent than an established cell line. An example of a cell culture system that can be used for testing uses human lens epithelial (HLE) cells. HLE cells from derived from whole eyes or anterior lens tissue removed during extracapsular cataract extraction can be grown as a primary culture. Preferably the cells are grown on the surface of the donor's original lens capsule attached to collagen coated tissue culture wells. Any variability in testing of the cytotoxic agents can be reduced by dissecting each lens capsule into smaller segments, for example into quarter or half segments, which are then exposed to the control or test substance. The effects of the analytes can then be evaluated by assessing cell viability and function. Various tests can be used to determine these parameters: examples include trypan blue dye exclusion for assessing cell viability and incorporation of radioactive amino acids for example tritiated leucine, into protein. The cultured HLE model offers the advantage that the cells are not immortalized or transformed and therefore may have a metabolism closer to that of HLE in vivo. Major differences in sensitivity between the test system and cells in vivo are thus minimized allowing for a more accurate determination of the dose of cytotoxic agent needed to kill the intended target cells.

In using the subject invention, a sufficient amount of the cytotoxic agent will be introduced into the anterior chamber and/or posterior chamber and/or residual lens capsule of the eye following lens removal to inhibit proliferation of any remnant lens epithelial cells. Methods for introducing the cytotoxic agent include injection directly into the posterior chamber of a solution comprising the cytotoxic agent and for example, bound covalently or noncovalently to an intraocular lens as described in U.S. Ser. No. 488,323 filed Mar. 6, 1990. This application is hereby incorporated by reference.

The cytotoxic agent can also be introduced following introduction of a non-cytotoxic agent capable of specifically binding to sites crossreactive with the cytotoxic agent. Non-cytotoxic agent, 10–100 μg, preferably 20–500 μg in 10–20 μl, is injected intracamerally through the limbus. For the most part, this agent will be a monoclonal antibody or a specific binding fragment thereof. Generally the solution will be a physiologically acceptable solution, which may be saline, phosphate-buffered saline or the like.

Other methods of introduction can include for example instillation of the non-cytotoxic agent following incision of the cornea and instillation of about 25–200, preferably about 50–150, more preferably about 100 μl of a non-cytotoxic agent capable of specifically binding to sites cross-reactive with the cytotoxic agent. The antibodies or fragments thereof will bind to all sites which may be cross-reactive with the cytotoxic agent and will also bind non-specifically to "hot spots" which may be present within the anterior chamber of the eye. In this way, the cells will be protected from the subsequent application of cytotoxic agent.

The use of the cross-reactive binding agent will be of particular importance where the cytotoxic agent has cross-reactivity, either specific or non-specific, with cells other than lens epithelial cells. By use of the prior instillation of the cross-reactive non-cytotoxic binding moiety, cytotoxic agents may be prepared which cross-react to varying degrees with cells, particularly epithelial cells, other than lens epithelial cells.

After allowing for antibody binding, generally 2–5 min, but up to 10–15 min, a corneal incision is made (see for example *Extracapsular Cataract Surgery*, Emery & Mcintyre, Mosby Company, St. Louis, 1983) and the anterior chamber flushed with a physiologically acceptable solution such as a balanced salt solution to remove any unbound non-cytotoxic agent. Extracapsular surgery, lens removal and intraocular lens instillation is performed according to standard methods (Emery & McIntyre, supra). After the corneal incision is closed, a second injection is made into the lens capsule area or directly into the residual lens capsule, if at least substantially intact. The material for the second injection comprises a cytotoxic composition and generally will comprise 10–20 μl, but may be up to 200 μl or up to 500 μl as necessary, to provide an amount of the cytotoxic agent sufficient to substantially completely or completely kill all of the lens epithelial cells, usually about 1–10 μg.

Generally, the cytotoxic effect of inhibition of protein synthesis will be realized within a relatively short time after binding of the cytotoxic agent to the cells, generally 0.5–15 hours, depending upon the concentration of the cytotoxic agent used. Where the method of introduction is in conjunction with, for example an intraocular device, the rate of release of the cytotoxic agent from the intraocular device will also effect the time elapsed before a cytotoxic effect is achieved. The observation of cell death as a result of inhibition of protein synthesis may take several days, generally 5–15 days, or longer.

The clinical development of secondary cataract may take from a few months to several years. Secondary cataract is in human patients determined by slit lamp microscopy, and presents as the appearance of lens epithelial cells growing on the posterior lens capsule. The invention described herein provides for exposure to the lens epithelial cells specific cytoxic agents that would destroy these cells and hence prevent their proliferation. Thus, slit lamp microscopy can be used to determine that development of a secondary cataract has not occurred. The subject compositions can be provided as kits for use in one or more operations. The kits will include the non-cytotoxic agent and the cytotoxic agent, either as concentrates (including lyophilized compositions), which may be further diluted prior to use or at the concentration of use, where the vials may include one or more dosages. Conveniently, single dosages may be provided in syringes, contained in sterilized containers, so that the physician may employ the syringes directly, where the syringes will have the desired amount and concentration of agents. Thus, the kit may have a plurality of syringes containing the cytotoxic agent as well as the non-cytotoxic agent in appropriate proportional amounts. Where the syringes contain the formulation for direct use, usually there will be no need for other reagents for use with the method.

The following examples are offered by way of illustration and not by way of limitation.

EXPERIMENTAL

Murine hybridoma cell line HBI-4197-X, which secretes an $IgG_3$ antibody at least substantially specific for lens epithelial cells, was deposited with the ATCC on Jun. 14, 1988 and was given ATCC Accession No. HB 9747.

EXAMPLE 1

Preparation of Monoclonal Antibodies

A. Immunization

Mice (BALB/c) were immunized with human cervical carcinoma epithelial cells (ME180) by injecting i.p. about $5 \times 10^6$ cells/200 μl three times over 2 week intervals and i.v. 3 days before isolation of the spleen with $5 \times 10^6$ cells/200 82 l. Additional mice (BALB/c) were immunized with human lens epithelial cells, obtained following cataract surgery, emulsified in Freunds Complete Adjuvant. About $5 \times 10^5$ cell equivalents/200 μl were given per animal for the primary injection. Additional injections consisting of equivalent cell material emulsified in Freunds incomplete were given i.m. 3 weeks apart. These mice received two additional injections of either ME180 cells or human amnion cells (WISH) prior to harvesting spleens for fusion.

B. Fusion

Spleens from immunized animals were removed three to five days following the last injection and prepared as a single cell suspension. The lymphocytes then were fused with P3-X-63/Ag8.653 mouse myeloma cells under conventional conditions. See U.S. Pat. No. 4,432,751, which disclosure is incorporated herein by reference. Following fusion, the cells were resuspended in Iscoves medium containing hypoxanthine, aminopterin, and thymidine (HAT medium) and placed in wells according to the number of myeloma cells to give a density of about $10^4$ cells/well. The cells were fed on days 5, 12, and 15 by removing and replacing half of the medium. Cultures identified as positive for antibody secretion by screening assays, were transferred to 24-well plates containing 1 ml Iscoves medium containing hypoxanthine and thymidine (HT).

C. Screening (i) ME180 immunization:

For screening, the hybridoma supernatant (100 μl) and 100 μl ME180 cells ($2 \times 10^5$ cells/ml) were incubated at 4° for one hr and then at 37° overnight in 96-well microtiter plates. The wells were viewed microscopically to detect disturbances (disturbed adhesion). Cells showing signs of disturbance were isolated and cloned 3 times. One of the hybridomas testing positively was designated 3D4. 3D4 produces an $IgG_1$ monoclonal antibody as determined by gel diffusion using isotype specific antiserum.

(ii) HLE/ME180 immuization:

For screening, hybridoma supernatants were tested for binding to ME180 cells by ELISA. Bound mouse immunoglobulin was detected by goat anti-mouse IgG-horse radish peroxidase. One of the hybridomas testing positively was designated 4757. This hybridoma produces an $IgG_1$, as determined by gel diffusion.

(iii) HLE/WISH immunization:

For screening, hybridoma supernatant was tested for binding to WISH cells by ELISA. Bound mouse immunoglobulin was detected as described. One of the hybridomas testing positively was designated 4197-X. This hybridoma produces an $IgG_3$ antibody as determined by gel diffusion.

(iv) Human lens epithelial cell antigen:

Hybridoma supernatants from fusions performed with spleen cells obtained from human lens epithelial cell immunized mice were tested by ELISA. Ninety-six well plates were coated with a Nonidet P-40 soluble fraction of human lens epithelial cells obtained following cataract surgery.

Fifty microliters per well of this soluble fraction were added to 96-well plates, dried and fixed with 0.05% glutaraldehyde for 15 minutes at 25° C. The plates were washed and incubated with cell culture medium containing 10% FBS for 60 minutes at room temperature. (Kelleher, et al., *Cancer Immunol Immunother* (1983) 14:185–190 and Mujoo et al., *J. Biol. Chem.* (1986) 261:10299–10305). Hybridoma supernatants, 100 µl/well, were added to the wells and incubated for 60 minutes. The wells were then washed and bound antibody detected by goat anti-mouse IgG-horseradish peroxidase. Cultures testing positive were expanded to 24 well plates and tested further for cellular binding specificity.

D. Cell Binding of Monoclonal Antibody

Supernatants from hybridomas 3D4, 4197-X and 4757 were tested by ELISA for ability to bind to both normal and tumor cells. Adherent cell lines were grown to confluence in 96-well plates and then fixed with 0.05% glutaraldehyde for 10 minutes. Suspension cultures were attached to poly L-lysine coated plates and fixed as above. Monoclonal antibody in culture medium was added to the wells and incubated at 37° C. for 1 hour. The plates were washed

TABLE 1

Binding of 3D4, 4197-X and 4757 Antibodies to Various Cell Types

| Cell Line | Tissue | Cell Type | Absorbance at 450 nm* | | |
|---|---|---|---|---|---|
| | | | 3D4 | 4197-X | 4757 |
| ME180 | human cervix | epithelial | 0.40 | 0.17 | 0.28 |
| WISH | human amnion | epithelial | 0.21 | 0.16 | 0.16 |
| COLO 320 | colon | adenocarcinoma | 0.01 | 0.00 | 0.00 |
| MRC5 | human skin | fibroblast | 0.14 | 0.06 | 0.03 |
| Daudi | Burkitt lymphoid | lymphoma | 0.01 | 0.07 | 0.02 |
| Y79 | retinoblastoma | | 0.01 | 0.06 | 0.00 |
| RPMI 7932 | melanoma | melanoma | 0.03 | 0.00 | 0.00 |
| RLE | rabbit lens | epithelial | 0.70 | 0.00 | 0.43 |

*Absorbance at 450 nm: Increasing absorbance reflects increased binding of antibody to cells.

three times and bound mouse IgG detected with goat anti-mouse IgG conjugated to horseradish peroxidase. Binding of the monoclonal antibodies to various cell types is shown in Table 1, above.

The antibodies prepared using human cervical carcinoma cells or other epithelial cells as an immunogen are capable of binding to rabbit lens epithelial cells, as well as epithelial cell lines derived from a variety of different tissues. There is little or no binding to cells of non-epithelial origin. In addition, the antibodies from 3D4, 4197-X and 4757 bind to human lens epithelial cells as shown by immunocytochemical staining. These results are shown in Table 2.

TABLE 2

Binding to HLE cells*

| | Antibody | | |
|---|---|---|---|
| | 3D4 | 4197-X | 4757 |
| Relative staining | ++ | +++ | ++ |

*Media control, or irrelevant antibodies did not stain human lens epithelial cells.

Concomitant addition of $^{125}$I-3D4 and excess unlabeled 3D4 to the cells in culture inhibited the binding of the labeled 3D4 by 90%. These results are shown in Table 3.

TABLE 3

Specificity of Binding of $^{125}$I-3D4 to Epithelial Cells

| | CPM $^{125}$I | |
|---|---|---|
| Addition | RLE* Cells | ME180 Cells |
| $^{125}$I-3D4 in buffer control | 4480 | 2470 |
| $^{125}$I-3D4 in excess 3D4IgG | 460 | 400 |
| % Inhibition | 90% | 84% |

*RLE = rabbit lens epithelial cells

EXAMPLE 2

Preparation of Toxin-Antibody Conjugates

A. Preperation Toxin A-Chain (i) Diphtheria Toxin: Fragment A (DTA) is prepared from diphtheria toxin (ICN Biomedicals Incorporated) as described (Chung and Collier, *Biochem. Biophys. Acta* (1977) 483:248–257) and is heated to 80° C. for 10 minutes to inactivate any residual traces of toxin. Enzymic activity of DTA is assayed by ADP-ribosylation of wheat germ elongation factor 2 with $^{14}$C-AND as substrate.

(ii) Ricin Toxin: Ricin toxin was purified from castor beans (A. H. Hummert Seed Co., St. Louis, Mo.) by affinity chromatography on Sepharose 4B. (Nicolson and Blaustein, ibid. (1972) 266:543–54). Ricin toxin A-chain (RTA) was purified from whole ricin toxin by reduction from 2-mercaptoethanol and chromatography on Cellex-D (Bio-Rad) (Olsnes and Pihl, *Biochem.* (1973) 12:3121–3126). RTA is freed of residual traces of ricin toxin by repeated cycling on Sepharose 4B columns.

(iii) Ricin A Chain (alternative preparation): Ricin A chain is purified as described by Vidal, H. et al., *Int. J. Cancer* (1985) 36:705–711. Briefly, ground, unshelled castor seeds (A. H. Hummert Seed Co.) are defatted with diethyl ether and the ether removed by filtration. The insoluble material is suspended in distilled water acidified to pH 4.0 with HCl and extracted by stirring for four hours. The crude extract is chromatographed on a CM-cellulose column equilibrated with 10 mM sodium acetate buffer, pH 4.0 and the ricin-containing fraction eluted with 100 mM Tris-HCl buffer, pH 8.0 containing 100 mM NaCl. The ricin fraction is then applied to an agarose gel (Sepharose 4B) column equilibrated with 10 mM phosphate buffer pH 6.5. The ricin is eluted from the column with a linear 0–500×10$^{-6}$M galactose gradient. The ricin is then applied to a CM 52 cellulose column equilibrated with 10 mMphosphate, pH 6.5 and the ricin-containing fraction eluted with 10 mM phosphate, pH 6.5 buffer containing 30 mM NaCl. The ricin is then isolated (desalted, etc). One gram of ricin is then reduced in 200 ml 100 mM Tris HCl buffer, pH 8.4 containing 2.5% 2-mercaptoethanol. After standing for one hour, the solution is applied to a DEAE-Sepharose column equilibrated with 100 mM Tris HCl pH 8.4. The column is washed with this buffer until the unabsorbed protein (A chain) is eluted as measured by absorbance at 280 nm. The purified ricin A is concentrated by ultrafiltration, dialyzed against 50 mM Tris-HCl pH 8.0 and stored at 4° C. until use.

B. Synthesis of Toxin-SS Antibody Conjugates (i) Synthesis of (DTA)-SS antibody conjugates:

Antibody 3D4 (7.0 ml, 2 mg/ml) is dialyzed against Dulbecco's phosphate buffered saline (DPBS Gibco), pH 7.4, containing antibiotic-antimycotic solution (Gibco, 5.0 ml/l). N-succinimidyl-3-(2-pyridyldithio)propionate (SPDP) (0.186 ml, 10 mM) in absolute ethanol is added to the antibody with vigorous mixing. The mixture is allowed to react for 30 min at room temperature and then dialyzed against two 1-liter changes of the same buffer. After dialysis the antibody preparation is analyzed for 2-pyridyldisulfide content as described (Stuchbury et al., *Biochem. J.* (1975) 151:417–432). DTA (3.0 ml, 2.5 mg/ml) is reduced by addition of 0.3 ml of 1.0M dithiothreitol, pH 7.0, for 30 min at room temperature and desalted on Sephadex G-25 (2.6×12 cm column) equilibrated with the buffer described above. Peak fractions from the column are pooled (11.0 ml, 0.53 mg/ml) and mixed with PDP-(3D4) antibody (7.0 ml, 2.1 mg/ml). Final concentration of DTA and antibody are $15 \times 10^{-5}$M and $55 \times 10^{-6}$M respectively. The final molar ratio of DTA to antibody in the reaction mixture is about 3. The crude conjugate preparation (18.0 ml) is concentrated to a final volume of 0.9 ml by ultracentrifugation on an Amicon YM-10 membrane. Crude (DTA)-SS-(3D4) (9.0 ml) is chromatographed on a Sephacryl S-200 column (2.6×106 cm, 22.1 ml/h flow rate) equilibrated with DPBS buffer. Each fraction (6.2 ml) is analyzed for ADP-ribosylation activity and by sodium dodecylsulfate/polyacrylamide gel electrophoresis (SDS/PAGE). Fractions containing the conjugate as determined by $A_{280}$ and bioactivity are pooled, concentrated on an Amicon YM-10 membrane, and are used in cytotoxicity assays after filter sterilization.

(ii) Synthesis of (RTA)-SS-(3D4) antibody conjugate: (RTA)-SS(3D4) was synthesized as described by Kernan et al. *J. Biol. Chem.* (1984) 133:137–146. Briefly, 3D4 (1 to 2 mg/ml) was dialyzed against 0.1M NAPO$_4$, 0.1M NaCl, pH 7.7, and 5–10 fold molar excess of N-succinimidyl-3-(2 pyridyldithio)propionate (SPDP) was added to the antibody with vigorous mixing. After incubation at room temperature for 30 min the pyridyldithiopropionate (PDP)-modified antibody solution was dialyzed against two changes of PBS. After dialysis, the PDP group to antibody ratio was determined. RTA was initially reduced by the addition of dithiothreitol at a final concentration of 50 mM, followed by incubation for 1 hour at room temperature. The RTA was then dialyzed extensively against PBS (4° C.) to remove any residual reducing agent. The RTA was then concentrated by using an Amicon stirred cell fitted with a YM10 membrane to a final concentration of 4 mg/ml. A five to ten fold molar excess of RTA was then added to the PDP-antibody solution and the mixture incubated for 16 hrs at 4° C. The RTA-3D4 conjugate was purified by chromatography on Sephacryl S-200.

(iii) (RTA)-SS-4197X was synthesized as described by Kernan et al. *J. Biol. Chem.* (1984) 133:137–146 with modifications. Briefly, 4197X antibody (1–2 mg/ml) was prepared in 100 mM sodium bicarbonate, 500 mM sodium chloride, pH 8.0 buffer. A 7.5-fold molar excess of N-succinimidyl-3-(2-pyridyldithio)propionate (SPDP), dissolved in absolute ethanol, was added to the antibody solution with vigorous mixing. After incubation at room temperature for 60 minutes the pyridyldithiopropionate (PDP)-modified antibody solution was passed over a Sephadex G-25 column equilibrated with 100 mM sodium bicarbonate, 500 mM sodium chloride, pH 8.0. The PDP group to antibody ratio was determined. Ricin A chain was initially reduced by the addition of dithiothreitol to a final concentration of 50 mM, followed by incubation for 30 min. at room temperature. The ricin A chain was then passed over a Sephadex G-25 column equilibrated with 100 mM sodium bicarbonate, 500 mM sodium chloride, pH 8.0 to remove any residual reducing agent. Five-fold molar excess of ricin A chain was then added to the PDP-antibody solution and the mixture incubated for 16 hours at 4° C. The 4197X-ricin A conjugate was purified by affinity chromatography on protein A-agarose and ion-exchange chromatography on S-Sepharose fast flow. After loading with immunotoxin, the protein A affinity column was washed with 100 mM Tris-HCl pH 8.00 containing 275 mM sodium chloride at pH 8.0 and eluted with 100 mM sodium acetate, pH 4.15 containing 275 mM sodium chloride. The eluted immunotoxin was applied to the S-sepharose fast flow column. It was eluted from the column with 100 sodium acetate pH 4.15 containing 500 mM sodium chloride. It was finally passed over a Sephadex G-25 column equilibrated with 100 mM sodium bicarbonate, 500 mM sodium chloride, pH 8.0 and stored at 4° C.

C. Preparation of Saporin-Antibody Conjugates (i) Isolation of Saporin

Saporin was extracted from the seeds of *Saponaria officinalis* using 0.14M NaCl, 5 mM NaPO$_4$, 10 pH 7.2, using 8 ml/g, by soaking the ground seeds overnight at 4° C. The supernatant was removed and centrifuged at 28,000×g for 30 min. The crude supernatant was dialyzed against 5 mM NaPO$_4$, pH 6.0, then purified by passage over a CM ion exchange column from which the saporin was eluted with an 0.0–0.3 NaCl gradient (linear). Fractions having ribosome-inhibiting activity were pooled and dialyzed against phosphate buffered saline (PBS) using the method of Stirpy et al., *Virchows Arch.* (1987) 53:259–271.

D. Conjugation

Purified antibody is treated with N-succinimidyl-3-(2-pyridyldithio)propionate (SPDP) for 30 min at room temperature then dialyzed against PBS to remove any unreacted SPDP groups. After dialysis the antibody preparation is analyzed for 2-pyridyldisulfide content as described in Example 2.B supra. The ratio of antibody to SPDP is 10- to 15-fold excess of SPDP to antibody. The saporin is treated with a 10-fold excess of SPDP in PBS, pH 7.0, for 30 min at room temperature then desalted on Sephadex G-25 as described in Example 2.B. Peak fractions from the column are pooled and mixed with PDP-antibody in a ratio of 5-fold molar excess of saporin to antibody. The conjugates are purified by passage over a Sephacryl-300 column. Fractions having a molecular weight in the range of about 160–210 Kd MW are collected and tested for immunological specificity and cytotoxicity.

EXAMPLE 3

Effect of 3D4-Ricin A Conjugates on Target Cells

A. Cytotoxicity

Target cells (ME180, RPMI 7932; rabbit lens epithelial cells (RLE)) were plated in 96-well plates to achieve 25% confluence. Ricin A-conjugate (stock solution 1 mg protein/ml) or control media was added at the indicated dilutions and incubated for 10 min at either 37° or 25° C., The supernatant was removed, the cells washed twice and fresh medium without toxin conjugate added to the wells. The plates were incubated at 37° C. until control wells were confluent. Cell density then was determined by conversion of the yellow dye 3-(4,5-dimethylthiazol-2-yl)-2,5-diphenyl tetrazolium bromide (MTT) to a purple product by living cells in direct proportion to cell number and metabolic activity. Appearance of the product was measured spectrophotometrically. Mosmann, *J. Immunol. Methods* (1983) 65:55, Percent reduction in cells was calculated by:

% reduction in cells =

$$100 - \frac{\text{Cell density (absorbance) in test}}{\text{Cell density (absorbance) in control}} \times 100$$

The results are shown in Table 4, below.

Proliferation of specific target epithelial cells was significantly prevented by exposure to as little as 10 μg protein/ml of 3D4-ricin A conjugate, a concentration which had no effect on RPMI 7932 control cells.

TABLE 4

Cytotoxicity of 3D4-ricin A for Cells:
10 minute incubation at 37° and 25° C.
Percent Reduction in Cells

| 3D4-ricin A | Cell Type | | | | | |
|---|---|---|---|---|---|---|
| Conjugate | ME180 | | RPMI 7932 | | RLE | |
| Dilution | 37° C. | 25° C. | 37° C. | 25° C. | 37° C. | 25° C. |
| 1:10 | 93 | 88 | 24 | 0 | 84 | NT* |
| 1:20 | 96 | 88 | 18 | 0 | 85 | |
| 1:40 | 95 | 88 | 6 | 0 | 84 | |
| 1:80 | 91 | 87 | 15 | 11 | 85 | |
| 1:160 | 81 | 74 | 9 | 11 | 83 | |
| 1:320 | 53 | 53 | 0 | 4 | 84 | |
| 1:640 | 39 | 42 | 0 | 0 | 80 | |
| 1:1280 | 24 | 10 | 2 | 0 | 70 | |
| 1:2560 | 11 | 8 | 5 | 0 | 60 | |
| 1:5120 | 1 | 0 | 15 | 0 | 59 | |

*NT - Not tested

B. Inhibition of Growth

Human lens epithelial cells obtained from cataract surgery were incubated in RPMI 1640 containing 10% FBS. For the experiment, the culture medium was removed and replaced with 3D4 RTA immunoconjugate in medium (20 μg/ml) or medium alone for 6 hours at 37° C. Following this incubation, cells were washed and given fresh culture media without conjugate and incubated for 48 hours. $^3$H-leucine was added to all cultures 24 hours prior to harvest of TCA precipitable protein. Thorpe et al., *Eur. J. Biochem* (1981) 116:447; Domingo and Trowbridge, *Methods in Enzymology* (1985) 112:238; Vitetta et al., *Proc. Nat. Acad. Sci. (USA)* (1983) 80:6332. The results are shown in Table 5.

TABLE 5

Inhibition of $^3$H-leucine Incorporation by
Human Lens Epithelial Cells by 3D4-ricin A

| Culture Addition | CPM Incorporated |
|---|---|
| 3D4-Ricin A | 3,655 |
| Medium Alone | 22,255 |

These data suggest that the monoclonal antibodytoxin conjugate is being translocated into the lens epithelial cell where the cytotoxic portion is active.

EXAMPLE 4

Inhibition of Cytotoxic Effect of Conjugate by
Prior Incubation With Unconjugated Monoclonal
Antibody To demonstrate protection of cross-reactive cells which bind the conjugate specifically, unconjugated 3D4 or medium alone was added to the cultures 10 min. prior to 3D4-ricin toxin A conjugate addition. A dilution of conjugate (as indicated in Table 6) was then added to the cells, incubated for 60 min. at 37° C. Cells were then washed and given fresh medium and incubated for 3 days at 37° C. Cell density was determined with MTT as described above (See Example 2).

TABLE 6

Effect of Preincubation of Cells
With Unconjugated Monoclonal Antibody[1]

| | | Treatment | |
|---|---|---|---|
| 3D4 RTA (X 100) | μg/ml[2] | 3D4 RTA | 3D4 IgG + 3D4 RTA[3] |
| 2 | 5.0 | 10 | 67 |
| 4 | 2.50 | 21 | 95 |
| 8 | 1.25 | 20 | 99 |
| 16 | 0.62 | 32 | 98 |
| 32 | 0.31 | 50 | 98 |
| 64 | 0.16 | 60 | 98 |
| 128 | 0.08 | 91 | 98 |
| 256 | 0.04 | 87 | 98 |
| 512 | 0.02 | 100 | 100 |

[1]Expressed as a percentage of control cells not treated with conjugate.
[2]Stock solution 3D4-RTA made up at 1 μg/ml.
[3]Cells were exposed to 3D4 IgG at 100 μg/ml for 10 minutes. Cells were washed 3 times and 3D4 RTA added.

EXAMPLE 5

Effect of Conjugate on Proliferation of Rabbit Lens
Epithelial Cells in vivo

Female New Zealand White rabbits, 3 kg, underwent extracapsular lens removal under general anesthesia (Emery et al., (1983) supra). Prior to surgery, animals received an injection of 3D4 IgG in 3° balanced salt solution (BSS) (Alcon Labs, Fort Worth, Tex.) into the anterior chamber. Anterior capsulotomy was performed and the lens extracted with a Kelman phacoemulsifier (Cooper Vision, Irvine, Calif.). Lens material was aspirated/irrigated from the eye with BSS. Just before closure, 200 μl of immunoconjugate or BSS was injected into the anterior chamber. Eyes were treated externally with broad spectrum antibiotic ointment and steroids. Eyes were examined for evidence of remnant lens epithelial cell proliferation.

EXAMPLE 6

Immunotoxin Effects in vitro on Human Lens
Epithelial Cells Grown on Original Lens Capsule HLE cells were grown in tissue culture on the surface of the original lens capsule. The reestablishment of the HLE cell layer on the capsule served as a model for the proliferation of these cells during the process of secondary cataract formation. Using this model, the cytotoxicity of monoclonal antibody 4197X-ricin A chain immunoconjugate (4197X-RA) on HLE cells in culture was determined.

A. Source of Tissue

Lens tissue was obtained from several sources.

1. Eyes were obtained from the Lions Eye Bank (Houston, Texas) within 24 hours of the time of death and held at 4° C. prior to treatment. Data from these lens specimens are given in Table 7, below. Each eye was cut equatorially to free its anterior segment from the posterior eye. The intact lens with its surrounding capsule was removed to a plastic petri culture dish containing 1 ml of RPMI 1640 medium. The lens was divided in half along the central axis perpendicular to its equator. This procedure also causes the lens cortex to separate from the capsule in two pieces. The cortex pieces were discarded. Each half lens capsule was then cut along the original equator to produce equal quarter segments. Two of these quarter segments were immediately placed into 16 mm tissue culture wells each containing 1 ml of growth medium. The composition of the growth medium is given in Table 8, below.

surface. Cell viability was then determined by the methods described below.

2. Anterior lens capsule specimens approximately 6 mm in diameter were removed during extracapsular cataract extraction and immediately treated. Data from these specimens are given in Table 9. These lens specimens were treated essentially as described above for lens specimens

TABLE 7

Effects of Eighteen Hour Exposure of Immunotoxin and Ricin on HLE Cells

| Sample No. | Treatment | Concentration[1] (µg/ml) | Days in Culture | % Change in $^3$H-leucine Incorporation from Control | % Change in Trypan Blue Exclusion from Control |
|---|---|---|---|---|---|
| 1. | ricin | 5 | 5 | −99.9 | −96.0 |
| 2. | ricin | 5 | 7 | −99.8 | −100.0 |
| Mean ± SD (2 samples) | | | | −99.9 ± 0.1 | −98.0 ± 2.8 |
| 3. | 4197X-RA | 50 | 9 | −96.8 | −84.0 |
| 4. | 4197X-RA | 50 | 7 | −99.9 | −93.7 |
| 5. | 4197X-RA | 50 | 7 | −99.8 | −96.5 |
| Mean ± SD (3 samples) | | | | −98.8 ± 1.8 | −91.4 ± 6.6 |
| 6. | 4197X-RA | 5 | 14 | −100.0 | −100.0 |
| 7. | 4197X-RA | 5 | 7 | −70.9 | −56.8 |
| 8. | 4197X-RA | 5 | 8 | −74.3 | −87.3 |
| 9. | 4197X-RA | 5 | 8 | −98.9 | −100.0 |
| Mean ± SD (4 samples) | | | | −86.0 ± 15.6 | −86.0 ± 20.4 |
| 10. | 4197X-RA | 0.5 | 7 | −96.3 | −98.2 |
| 11. | 4197X-RA | 0.5 | 13 | −93.8 | −100.0 |
| 12. | 4197X-PA | 0.5 | 9 | −98.0 | −92.9 |
| Mean ± SD (3 samples) | | | | −96.0 ± 2.1 | −97.0 ± 3.7 |
| 13. | 4197X-RA | 0.05 | 14 | −99.5 | −100.0 |
| 14. | 4197X-RA | 0.05 | 8 | −93.9 | −84.9 |
| 15. | 4197X-RA | 0.05 | 6 | −98.2 | −100.0 |
| Mean ± SD (3 samples) | | | | −97.2 ± 2.9 | −95.0 ± 8.7 |
| 16. | 4197X-RA | 0.005 | 6 | −8.3 | −4.9 |
| 17. | 4197X-RA | 0.005 | 8 | 3.1 | 12.7 |
| 18. | 4197X-RA | 0.005 | 8 | −8.6 | −20.4 |
| 19. | 4197X-RA | 0.005 | 8 | 23.6 | 20.4 |
| Mean ± SD (4 samples) | | | | 2.5 ± 15.1 | 4.0 ± 21.3 |
| 20. | ricin A | 0.05 | 7 | −21.6 | −8.6 |

[1]Final concentration of 4197X-RA immunotoxin. intact ricin toxin, or purified ricin A chain were made by serial dilution into growth medium.

TABLE 8

Composition of Lens Growth Medium Utilized for the Cell Culture of Human Lens Epithelial (HLE) Cells (for 100 ml total volume)

95 ml of RPMI 1640 medium (without L-glutamine, Gibco)
5.0 ml of human serum (heat-activated, Sigma)
0.1 µg/ml of hEGF (human epidermal growth factor, Scott Labs.)
5.0 ng/ml of basic FGF (recombinant basic fibroblast growth factor, bovine, Amgen Biologicals)
5.0 µg/ml transferrin (human, Sigma)
5.0 µg/ml insulin (Scott Labs)
2.0 mM L-glutamine (Gibco)
20 mM HEPES (Sigma)
0.25 µg/ml Fungizone (Gibco)
100 U/ml of penicillin G and 100 µg/ml streptomycin sulfate (Gibco)

The other two segments were placed into wells containing dilutions of either immunotoxin (4197X-RA), intact ricin, or ricin A chain in growth medium. Wells were incubated at 37° C. in 95% air-5% CO$_2$. After 18 hours of incubation, the lens capsule segments were washed by dipping them in 4 consecutive wells of medium alone. Each segment was then placed, cell side up, at the bottom of a 16 mm well coated with type I collagen. Medium was added and the wells were incubated as described above for 5 to 14 days until the control cells reached ≧90% confluency on the capsule obtained from eyes except that the tissue was divided into equal halves (not quarters), with one-half incubated with immunotoxin (4197X-RA) for 6 hours while the other portion received only medium.

3. Anterior lens capsule specimens were also obtained after extracapsular extraction conducted at the Eye Center of Florida (Ft. Myers, Fla.). These specimens were each placed in sealed tubes in 1 ml of Modified McCarey-Kaufman Storage Medium containing 10% (v/v) fetal bovine serum and kept at 4° C. for 1 to 7 days prior to treatment. Data from these tissues are given in Table 10. These lens specimens were treated essentially as described above except that control and treatment segments were incubated for 2 hours.

B. Determinations of the Effects of Immunoconjugates on Growth and Viability of HLE Cells on Explanted Lens Capsules After a suitable amount of time (5 to 14 days in tissue culture), to establish the viability of the control tissue specimens obtained as described above, it was possible to observe the effects of various treatments on cell viability. After the control cells reached ≧90% confluency, cell viability was determined by trypan blue exclusion or 3H-leucine (L-(4,5-$^3$H) leucine, 130–140 Ci/nmol in aqueous solution; Amersham) incorporated into protein. These procedures are described below. The determination of 3H-leucine incorporation into protein is a measure of the direct effects of immunotoxin on ribosomal protein synthesis. The use of a trypan blue dye exclusion as a vital stain is a standard technique for determining cell viability and is based on the fact that live cells with intact cell membranes exclude the dye and appear clear while cellular debris or dead cells stain blue due to the accessibility of the dye to intracellular protein. The acellular part of the lens capsule stains medium blue.

1. Trypan Blue Dye Exclusion Method.

Trypan blue staining solution (0.4%, Sigma) was added to each well to give a final concentration of 0.04% trypan blue. The staining solution was evenly distributed in the well by gently tapping the side of the tissue culture dish. The dish was then incubated for 15 minutes at 37° C. The morphology of the cells was noted using an inverted microscope and a field of 100 to 200 total cells enumerated under 100× magnification. The clear live cells were visually counted. In the same microscopic field, total cells (both clear and dark blue) were also counted. The percentage of viable cells was determined by dividing the number of clear cells by the number of total cells within the microscopic field.

2. $^3$H-Leucine Incorporated into Protein.

5 µCi of $^3$H-leucine in 0.5 ml fresh growth medium was added to each well and incubated for 18 hours. After 18 hours, the radioactive medium was removed. The cell contents were solubilized by the addition of 0.2 ml of a 1% (w/v) solution of sodium dodecyl sulfate (SDS). Trichloroacetic acid solution (TCA) was added to a 10% (w/v) final concentration to precipitate the cellular protein. The precipitate was collected by vacuum filtration onto glass fiber filters and washed extensively with 10% TCA. The filters were placed in glass vials with 10 ml Biofluor and counted in a liquid scintillation spectrometer.

Results of Eighteen Hour Exposure to Immunotoxin

Table 7 shows HLE cell viability after 18 hours of exposure to either ricin, immunotoxin 4197X-RA, or ricin A. The ricin was dosed at 5 µg/ml, immunotoxin from 0.005 to 50 µg/ml, and ricin A at 0.05 µg/ml. As can be seen from Table 8, ricin killed greater than 98% of the cells as measured by either $^3$H-leucine incorporation or trypan blue exclusion. The immunotoxin showed a dose dependent cytotoxic effect with the lowest effective dose being 0.05 µg/ml. Ricin A showed little cytotoxicity at 0.05 µg/ml.

Based on the data in Table 7, an IC$_{50}$ for 4197X-RA for 18 hours of treatment of HLE cells was 0.02 µg/ml for both inhibition of protein synthesis and trypan blue staining of the cells. This was calculated by extrapolating a 50% kill from a linear fit of percent inhibition plotted against the log of the immunotoxin concentration (r=0.69 and 0.66, respectively).

Results of Six Hour Exposure to Immunotoxin:

Table 9 (below) shows data on the viability of extracapsular cataract extraction lens specimens treated with 0.005 to 5.0 µg/ml of 4197X-RA immunotoxin. As in the 18 hour exposure, the immunotoxin exhibited a dose-dependent inhibition of cell viability with the lowest active dose being 0.05 µg/ml.

Based on the data in Table 10, an IC$_{50}$ for 4197X-RA for 6 hours of treatment of HLE cells was calculated to be 0.03 µg/ml for both inhibition of protein synthesis and trypan blue exclusion (r=0.74 and 0.75, respectively). This was slightly higher than what was found for 18 hour treatment of HLE cells with 4197X-RA immunotoxin.

TABLE 9

Effects of Six Hour Exposure of Immunotoxin on HLE Cells

| Sample | Treatment | Concentration[1] (µg/ml) | Days in Culture | % Change in $^3$H-leucine Incorporation From Control | % Change in Trypan Blue Exclusion From Control |
|---|---|---|---|---|---|
| 1 | 4197X-RA | 5 | 9 | −91.9 | −92.4 |
| 2 | 4197X-RA | 0.5 | 9 | −98.4 | −100.0 |
| 3 | 4197X-RA | 0.5 | 9 | −94.3 | −87.7 |
| 4 | 4197X-RA | 0.05 | 9 | −97.8 | −97.1 |
| 5 | 4197X-RA | 0.005 | 9 | 12.3 | 0.3 |

TABLE 10

Effects of Two Hour Exposure of Immunotoxin on HLE Cells

| Sample | Treatment | Concentration[1] (µg/ml) | % Change in $^3$H-leucine Incorporation From Control (Mean ± SD) | % Change in Trypan Blue Exclusion From Control (Mean ± SD) |
|---|---|---|---|---|
| n = 8 | 4197X-RA | 100.0 | −97.1 ± 2.1 | −100.0 ± 0.0 |
| n = 11 | 4197X-RA | 50.0 | −89.8 ± 10.5 | −96.1 ± 8.4 |
| n = 9 | 4197X-RA | 16.0 | −88.1 ± 0.79 | −90.9 ± 10.1 |
| n = 6 | 4197X-RA | 5.0 | −75.7 ± 22.9 | −79.3 ± 16.3 |
| n = 6 | 4197X-RA | 0.5 | −49.6 ± 32.1 | −54.9 ± 33.4 |
| n = 3 | 4197X-RA | 0.05 | −32.2 ± 19.6 | −18.3 ± 11.7 |

Results of Two Hour Exposure to Immunotoxin:

When extracapsular cataract extraction lens specimens were exposed for two hours to immunotoxin, inhibition of cell viability was less than that found for 6 and 18 hours of immunotoxin exposure. An 85% or greater inhibition of protein synthesis or inhibition of the exclusion of trypan blue dye was found for immunotoxin doses of between 16 and 100 µg/ml. A 90% or greater inhibition of these parameters was found for a dose range of approximately 50 to 100 µg/ml. Based on the data in Table 10, an IC$_{50}$ for 4197X-RA for 2 hours of treatment in HLE cells was calculated to be 0.38 µg/ml for inhibition of protein synthesis, and 0.54 µg/ml based on trypan blue staining of the cells (r=0.99 and 0.98 respectively for these parameters).

By introducing the subject cytotoxic agents, particularly after introduction of the non-cytotoxic binding moiety, remnant lens epithelial cells can be prevented from proliferating, thus avoiding secondary cataracts. The subject methods and compositions provide a simple procedure for preventing secondary cataracts while avoiding injury to other tissues in the eye and provide a safe alternative to the various techniques which have been used previously but which have general cytotoxic effects. By the subject two-stage treatment, a relatively non-specific cytotoxic agent (for example an antibody specific for epithelial cells) can be made specific for a certain epithelial cell population, lens epithelial cells. The unique anatomical location of the various epithelial cell types during cataract surgery renders the treatment method possible.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A method for inhibiting posterior lens capsule opacification after extracapsular cataract extraction from a host eye, said method comprising the step of:

introducing, in conjunction with said extracapsular cataract extraction, into at least one area of said eye selected from the group consisting of: the anterior chamber; the posterior chamber and the residual lens capsule in an amount sufficient to inhibit proliferation of lens epithelial cells, a cytotoxic agent capable of binding specifically to any lens epithelial cells preset in said area of the eye and killing the cells without additional agents, wherein said cytotoxic agent comprises a monoclonal antibody or fragment thereof conjugated to a toxin molecule or a cytotoxic moiety of a toxin molecule.

2. A method according to claim 1, wherein said method further comprises the step of:

introducing into at least one of the anterior chamber or posterior chamber of said eye, prior to said extracapsular extraction, a non-cytotoxic agent capable of binding to epithelial cells to which said cytotoxic agent is capable of binding.

3. A method according to claim 2, wherein said non-cytotoxic agent is a monoclonal antibody or fragment thereof.

4. A method according to claim 2, wherein said introducing comprises injecting said non-cytotoxic agent intracamerally through the limbus.

5. A method according to claim 1, wherein said cytotoxic moiety is an A chain of a toxin selected from the group consisting of: ricin; abrin; and diphtheria toxin.

6. A method according to claim 1, wherein said toxin molecule is saporin.

7. A method for preventing secondary cataract formation in Vivo following extracapsular cataract and lens extraction from a host eye comprising the steps of:

introducing through the limbus into the anterior chamber of said eye, prior to said extracapsular extraction, a monoclonal antibody or fragment thereof capable of binding specifically to epithelial cells present in said anterior chamber in an amount and for a time sufficient to bind to said epithelial cells;

removing any unbound monoclonal antibody or fragment thereof;

extracting said extracapsular cataract and lens from said eye;

injecting into the capsular area or a substantially intact residual lens capsule of said eye, in an amount sufficient to inhibit proliferation of any remnant lens epithelial cells, a cytotoxic agent capable of binding specifically to remnant lens epithelial cells present in said capsular area or residual lens capsule, wherein said cytotoxic agent comprises a monoclonal antibody or fragment thereof conjugated to a toxin molecule or a cytotoxic moiety of a toxin molecule, whereby at least said cytotoxic moiety is internalized by said remnant lens epithelial cells whereby said remnant lens epithelial cells am killed and secondary cataract formation is prevented.

8. A method according to claim 7, wherein said cytotoxic moiety is the A chain of a toxin selected from the group consisting of: diphtheria toxin; ricin; and abrin.

9. A method according to claim 7, wherein said cytotoxic moiety is saporin.

10. The method according to claim 7, wherein said introducing is by instillation through an incision in the cornea.

11. The method according to claim 7, wherein said introducing is by intracameral injection.

* * * * *

UNITED STATES PATENT AND TRADEMARK OFFICE
CERTIFICATE OF CORRECTION

PATENT NO.   :   5,616,122
DATED        :   April 1, 1997
INVENTOR(S)  :   Dominic M. Lam and Peter J. Kelleher It is certified that error appears in the above-indentified patent and that said Letters Patent is hereby corrected as shown below:

In the Title page, under Related U.S. Application Data, after "(63) Continuation-in-part of Ser. No.", insert --385,557, Jul. 29, 1989, Pat. No. 5,055,291, which is a division of Ser. No.--.

Column 1, line 5, before "204,168", insert --385,557, filed Jul. 29, 1989, now U.S. Pat. No. 5,055,291, which is a division of U.S. Ser. No.--

Signed and Sealed this

Thirtieth Day of June, 1998

Attest:

BRUCE LEHMAN

*Attesting Officer*      *Commissioner of Patents and Trademarks*